United States Patent [19]
Wilt et al.

[11] Patent Number: 6,100,528
[45] Date of Patent: Aug. 8, 2000

[54] ANALYTICAL QUANTIFICATION AND PROCESS CONTROL

[76] Inventors: Robert Wilt, 10075-1 Windstream Dr., Columbia, Md. 21044; George Eugene Toth, 8499 Hayshed La., Columbia, Md. 21045

[21] Appl. No.: 09/233,602

[22] Filed: Jan. 19, 1999

[51] Int. Cl.[7] .............................. G01N 21/47; G01J 5/08
[52] U.S. Cl. ................................. 250/341.2; 250/339.11; 250/341.8
[58] Field of Search .......................... 250/338.1, 338.5, 250/339.01, 339.06, 339.07, 339.1, 339.11, 339.12, 341.8, 341.1, 341.2, 358.1, 359.1; 358/300

[56] References Cited

U.S. PATENT DOCUMENTS

| | | |
|---|---|---|
| 4,801,804 | 1/1989 | Rosenthal . |
| 4,840,706 | 6/1989 | Campbell . |
| 4,957,770 | 9/1990 | Howarth ........................... 427/9 |
| 5,218,206 | 6/1993 | Schmitt et al. . |
| 5,220,168 | 6/1993 | Adamski et al. . |
| 5,343,045 | 8/1994 | Gupta . |
| 5,365,067 | 11/1994 | Cole et al. . |
| 5,424,545 | 6/1995 | Block et al. . |
| 5,635,402 | 6/1997 | Alfano et al. ..................... 436/63 |
| 5,637,873 | 6/1997 | Davis et al. . |
| 5,663,565 | 9/1997 | Taylor . |
| 5,747,813 | 5/1998 | Norton et al. . |
| 5,813,403 | 9/1998 | Soller et al. ...................... 128/633 |
| 5,818,339 | 10/1998 | Giles et al. . |
| 5,844,239 | 12/1998 | Kimura ............................ 250/341.8 |
| 5,879,075 | 3/1999 | Conner et al. .................... 362/551 |

*Primary Examiner*—Constantine Hannaher
*Assistant Examiner*—Albert Gagliardi
*Attorney, Agent, or Firm*—Law Offices of Royal W. Craig

[57] ABSTRACT

A method and device for high speed spectroscopic constituent verification. The method includes the steps of illuminating a sample with broadband light and measuring two preselected wavelengths of reflected light: a first narrow-range of wavelengths $\lambda 1$ that is not significantly absorbed by the constituent of interest, and a second narrow-range of wavelengths $\lambda 2$ that is substantially absorbed by the constituent of interest. Given the two measurements of reflection, upper and lower thresholds are determined (the latter based on a percentage of the measured baseline reflected light of wavelengths $\lambda 1$). Finally, the presence of the constituent of interest is indicated if the measure of the reflected discriminant wavelength $\lambda 1$ is within te upper and lower threshold measures of reflected baseline light $\lambda 1$. The compact device that implements the above-described method includes a base unit housing a near-IR discriminator circuit with a pair of selective light sensors, and a light source. A sensor unit connects to the base unit. The sensor unit includes a flexible neck with a connecting block attached at one end for mating with the base unit, and a hood assembly attached at the other end for enclosing a light collecting and transmitting lens. The optics are connected by an optical fiber bundle inside the flexible neck.

13 Claims, 5 Drawing Sheets

ANALYTICAL QUANTIFICATION AND PROCESS CONTROL

BACKGROUND OF THE INVENTION

1. Field of the invention

The present invention relates to sensors for process control and, more particularly, to an improved analytical discriminator for high speed spectroscopic constituent analyses.

2. Description of the Background

Many manufacturing processes involve the high-speed application of glue lines to articles such as paper sheets as they are conveyed past an applicator station. Modern automated gluers also include sensors to check the quality of the glue lines and to provide feedback for process control. For instance, in the context of making cardboard packaging, glue lines are applied to container blanks prior to folding. In such process, it is desirable to provide the process computer continuously with real time electrical signals that each glue line has been applied and is of the proper mix of constituents. However, these sensors must support extremely high-volume throughput (often in excess of 1000 sheets per minute). Thus, any analysis of the applied glue must be accomplished in real time, and the need for speed has greatly limited the types of analyses to simple (and largely unreliable) optical checks for the physical presence of glue.

Another more promising type of analysis is based on infra-red reflectance. Infra-red reflectance or spectroscopy has proven itself very useful in other industries and is capable of far more accurate and thorough analysis of constituents in a sample.

For example, U.S. Pat. No. 4,801,804 to Rosenthal shows a method and apparatus for near infrared reflectance measurement of a non-homogenous sample such as ground sunflower seeds. The sample is quantitatively analyzed by uniformly irradiating with near infrared radiation. A bifurcated optical fiber bundle is used with single source and return paths, and various (at least two) wavelengths of the reflected light are successively measured by an optical "chopper" and detector. The wavelengths are ratioed and compared to known values to give a direct reading of moisture content.

Likewise, U.S. Pat. No. 4,840,706 to Campbell shows an infra-red scanning gauge used in measuring the moisture content of a paper-web during manufacture. The scanner employs a measurement channel and a reference channel.

U.S. Pat. No. 5,218,206 to Schmitt et al. shows a method for determining the dryness, wetness, or icing of a road. The method employs reflection measurements of light in the infrared range. The reflected light is measured selectively and simultaneously by a receiver in at least two wavelength regions. A quotient of the detected signals determines the respective condition of the roadway surface. The two wavelength regions are selected to ensure that the quotient is indicative of either dryness, wetness., or icing.

U.S. Pat. No. 5,220,168 to Adamski et al. shows a method and apparatus for determining moisture content of materials by irradiating a sample with two wavelengths of light having different water absorptive characteristics (which are therefore reflected by varying degrees depending on the surface moisture on the material). The respective reflections are measured by a single common detector, and a value corresponding to the ambient light is subtracted from each measurement. A ratio of the resultant values is then correlated with data derived from precalibration measurements of samples of known moisture content.

U.S. Pat. No. 5,424,545 to Block et al. shows a non-invasive non-spectrophotometric method for measuring the blood glucose. A plurality of broad spectrum filters transmit beams of radiation in overlapping portions of the spectrum to the sample. Radiation reflected or transmitted by the sample is detected and decoded.

Theoretically, near-infrared reflectance technology is applicable to the context of paper and cardboard packaging as it is capable of substantiating that each glue line has been applied and is of the proper mix of constituents. based on the fact that infrared energy is known to be absorbed by typical glues at very specific wavelengths. That is, the absorptivity of infrared energy by glue is known to be dependent on wavelength. Specifically, using the conventional method, paper blanks moving along a conveyor belt would be illuminated under a reflection sensor. The reflected infrared energy power spectrum would be altered according to the characteristics of the glue (such as starch mass). The reflected light would be filtered by two or more narrow band pass filters of different wavelengths, inclusive of a first wavelength that is not readily absorbed by the glue and a second that is absorbed in the glue. By analyzing the relative reflected wavelengths the data is capable of giving a substantive quality check of the glue.

Unfortunately, the conventional analyses required to implement infra-red reflectance techniques as shown in the above-described prior art patents is complex and time-consuming, and there have been few successful efforts to adapt such techniques for the purpose of high-speed process control.

One known example is U.S. Pat. No. 5,663,565 to Taylor, which shows a system for determining glue-line, characteristics, such as temperature, of corrugated board. The output signal of an infrared absorption sensor provides an on-line starch measurement for corrugators. The incremental amount of infrared radiation that is absorbed by starch and/or water in the glue-lines is isolated from the predominant, more random background absorption due to cellulose and water in the paper substrate. The amplitude of the extracted signal component, which reflects only the starch and/or water in the glue, is then converted using empirically derived historical data.

Unfortunately, the analysis and implementing hardware used by the Taylor '565 patent is very cumbersome as the data must be compared and converted based on a database of historical data. As shown in the '565 patent, process control speed considerations require that a running average of glue readings be kept over time. The '565 method and device simply is not fast enough to operate in real time to provide a substantive analysis of each running glue line, and it would be greatly desirable to eliminate the need for averaging.

SUMMARY OF THE INVENTION

It is, therefore, an object of the present invention to provide an analytical discriminator for high speed spectroscopic constituent analyses for the industrial process control setting.

It is another object to provide an analytical discriminator as described above that is capable of an accurate and thorough analysis of constituents in a sample, for example, by a comparison of the amount of constituent with upper and lower thresholds.

It is another object to adapt the technique of near-IR reflectance to the context of high-speed process control in the paper and cardboard sheet gluer context to discriminate the starch and/or water in the glue.

It is another object to simplify the analysis and implementing hardware to provide a substantive analysis of each running glue line in real time, thereby eliminating the need for historical data or a running average of glue readings over time.

According to the present invention, the above-described and other objects are accomplished by providing a method and device for high speed spectroscopic constituent verification.

The method the steps of illuminating a sample with broadband light and measuring two wavelengths of reflected light. The reflected light is measured in a first narrow-range of wavelengths λ1 that is preselected as a baseline that is not significantly absorbed by a constituent of interest. The reflected light is also measured in a second narrow-range of wavelengths λ2 that is preselected as a discriminant which is substantially absorbed by the constituent of interest. Given the two measurements of reflection, upper and lower thresholds are determined based on a percentage of the measured baseline reflected light of wavelengths λ1. Finally, the presence of the constituent of interest is indicated if the measure of the reflected discriminant wavelength λ1 is within te upper and lower threshold measures of reflected baseline light λ1.

The device that implements the above-described method includes a base unit with an enclosure for housing a circuit board, and a near-IR discriminator circuit on the circuit board. The discriminator circuit has a pair of selective light sensors each responsive to a particular wavelength. A light source is positioned in the housing, and the base unit also includes a receptacle on the enclosure for completing at least three fiber optic couplings, two of the couplings leading to the respective light sensors and one to the light source. A sensor unit connects to the base unit. The sensor unit includes a flexible neck with a connecting block attached at one end for mating with the receptacle on said base unit enclosure and thereby completing the three fiber optic couplings. A hood assembly is attached at the other end of the flexible neck, the hood assembly encloses a light collecting and transmitting lens. The sensor unit also includes an optical fiber bundle for transmitting light through the flexible neck via a plurality of optical fibers. A first subset of the optical fibers in the bundle are coupled between the light source in the housing through said lens for illumination of the sample. A second and third subset of the optical fibers in the bundle are coupled between the lens and the light sensors for transmitting light reflected back from the sample to the base unit. The device carries out the above-described method whereby the near-IR discriminator circuit indicates the presence or absence of the constituent based on a difference in the reflected light received at the pair of selective light sensors.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

As stated above, the basic design concept embodied in the invention is an analytical discriminator and process control system that is physically as small an unobtrusive as possible, with a high-speed functional capability to make real-time go/nogo process control decisions based on the presence of a constituent in a sample within a range of acceptable thresholds.

Figure 1:
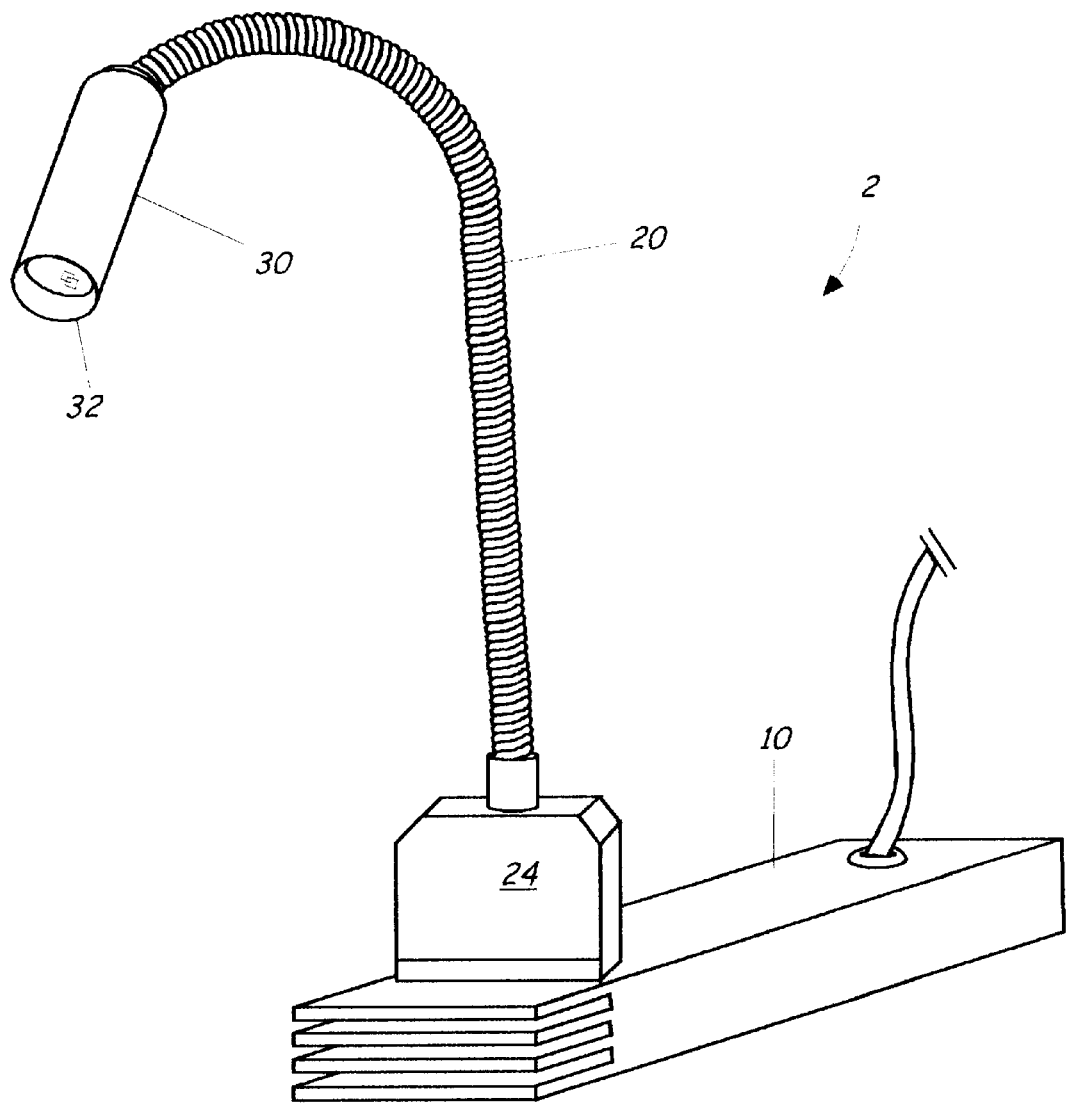
FIG. 1 is front perspective view of the analytical discriminator and process control system according to one embodiment of the present invention.

FIG. 1 is front perspective view of the analytical discriminator and process control system 2 according to one embodiment of the present invention. The discriminator 2 generally includes a lower base 10 for housing a light source and the discriminating circuitry (to be described), a hood assembly 30 for housing a light collecting and transmitting lens 32 (to be described), and a flexible neck assembly 20 mounted on a connecting block 24 for adjustably supporting hood assembly 30 a short distance from base 10. Flexible neck assembly 20 houses an optical fiber bundle that connects the hood assembly 30 to connecting block 24. Connecting block 24 in turn plugs directly into the lower base 10 to complete the requisite optical couplings to the light source, sensors and the discriminating circuitry housed therein. Physically, the dimensions of the lower base 10 measure approximately 2" by 1.2" by 6", the flexible neck 20 measures 18", and the hood assembly 30 is approximately 3" long with a ⅞" diameter.

Figure 2:
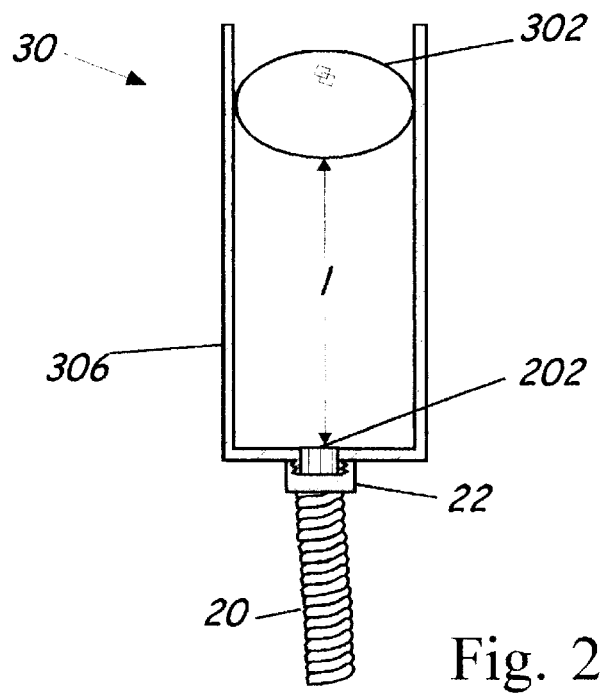
FIG. 2 is a side cross-section of the hood assembly 30.

FIG. 2 is a side cross-section of the hood assembly 30. Hood assembly 30 includes a hollow cylindrical casing 306 for housing and protecting a lens 302 seated therein. Casing 306 is open at one end for exposing lens 302. The optical fiber bundle 202 is routed through flexible neck 20, enters casing 306 through the other end, and is terminated a predetermined distance 1 from lens 302 as will be described. Optical fiber bundle 202 is preferably a commercially available bundle of 30–300 optical fibers (though as few as thirty will function, the preferred embodiment employs approximately three hundred). In accordance with the present invention, a random (incoherent) fiber bundle is used for both illumination and collection. The fiber bundle is made up of small cylindrical fibers packed together. In a random bundle the individual fibers are haphazardly located in the input and output (this is also known as "salt and pepper" fibers). Smaller fibers are more effective for the present application than larger core fibers.

The flexible neck 20 is terminated at a threaded collar 22 that mates with cylindrical casing 306. The entire optical fiber bundle 202 also terminates at the casing 306, the fibers being terminated and bonded by a stainless steel ferrule, and the ends being terminated (cut and polished flush) with a ferrule. The other end of fiber bundle 202 is trifurcated to effect three-way beam splitting, thereby providing an illumination path and two return paths from/to lower base 10. In an alternative embodiment, the other end of the fiber bundle is bifurcated to effect two-way beam splitting, thereby providing two return paths to the base 10 and the illumination is provided by a source 132A located external to the base 10.

Lens 302 is a preferably a bi-convex lens for imaging the sample to the fiber bundle. Proper imaging of the sample to the fiber bundle 202 to requires a choice of lens with two constraints. First, the focal length off the lens should be equal to both ½ the spacing 1 and ½ the distance from the lens to the intended sample. This ensures that the unmagnified sample image will be focussed onto the end of the fiber bundle 202. Second, the numeric aperture of the fibers in bundle 202 should be matched to the numeric aperture of the lens 302 as closely as possible. For the present application it is desirable to image a spot-size of $\leq 1$ mm. To accomplish this, it is necessary to employ at least 10 fibers in each of the beam-split paths, and the fibers should be approximately 150 micron core fibers. For lens 302, a 25 mm lens works well with a 0.5 mm spacing within the cylindrical casing 306, and an expected a 0.5 mm expected distance from lens to sample.

Figure 3:
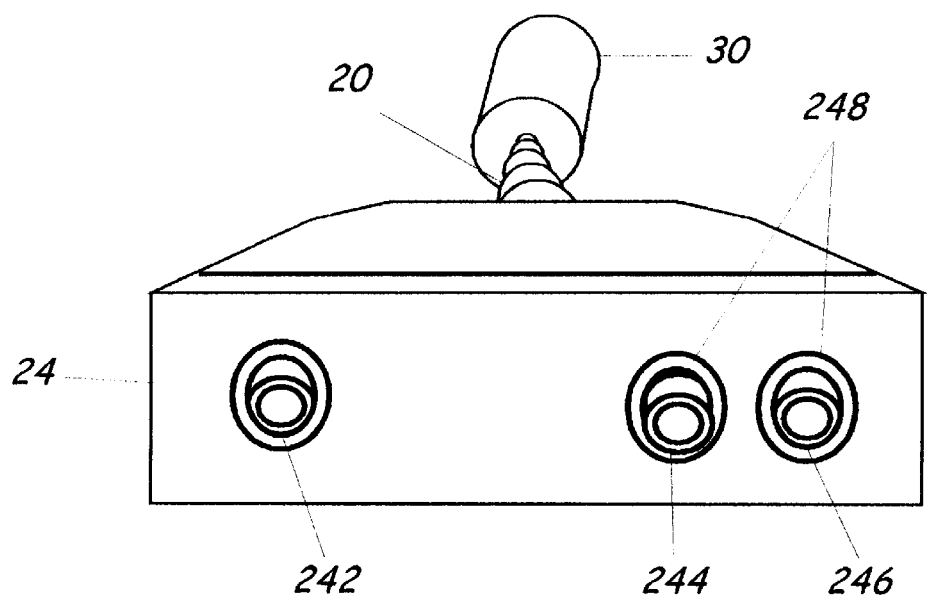
FIG. 3 is a bottom perspective view of the connecting block 24.
Figure 4:
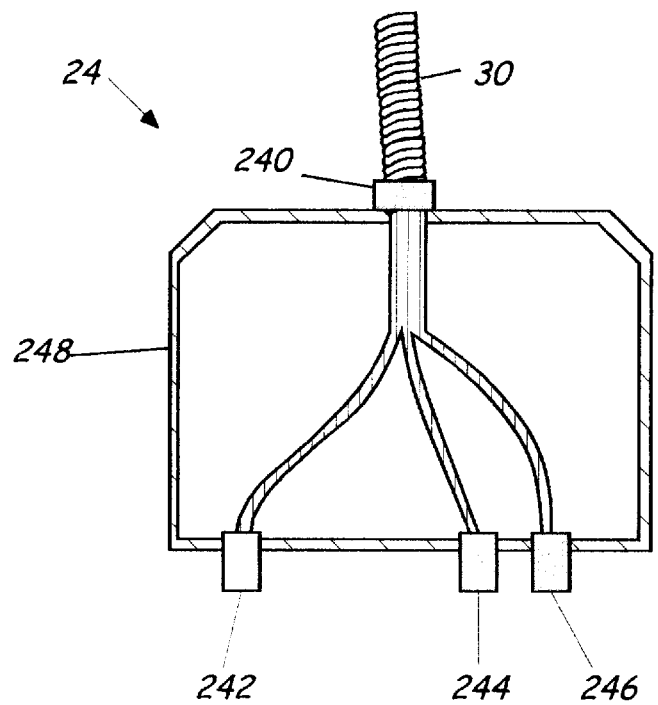
FIG. 4 is a side cross-section of the connecting block 24.
Figure 4A:
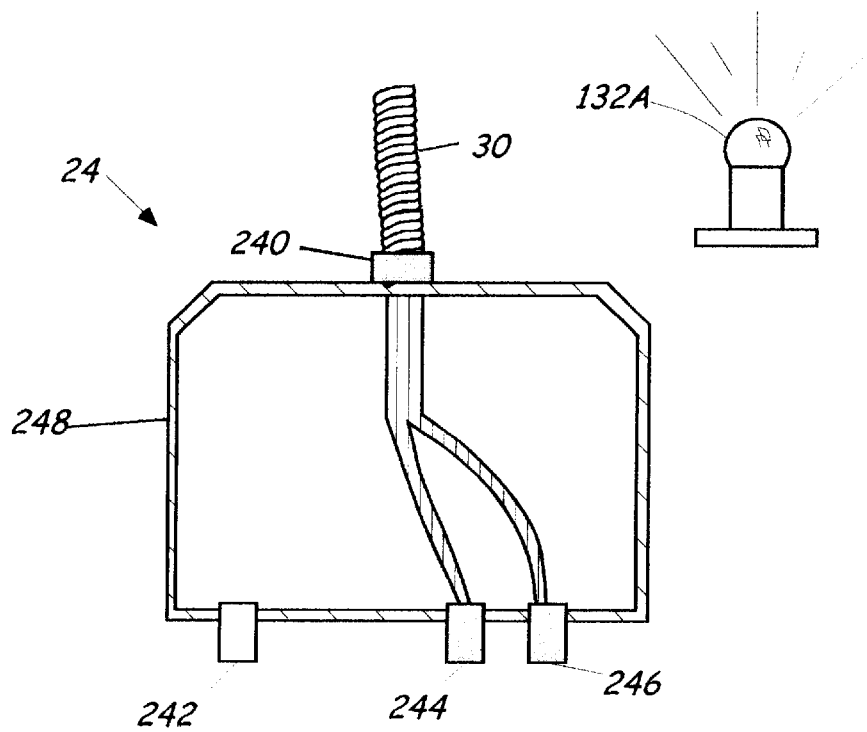
FIG. 4A is a side cross-section of an alternative embodiment of the connecting block 24.

FIG. 3 is a bottom perspective view and FIG. 4 is a side cross-section of the connecting block 24. Connecting block 24 includes a generally rectangular connector shell 248. Optical fiber bundle 202 is routed through flexible neck 20 and enters shell 248 through one end. The flexible neck 20 is terminated at a threaded collar 240 that mates with connector shell 248. Once inside connector shell 248, the fibers of bundle 202 are trifurcated and randomly divided into three groups. In the preferred embodiment, each of the beam split paths comprises a substantially equal number of individual fibers. One group continues through to a transmissive optical coupling 242 which transmits light from an illumination source in lower base 10 through lens 302 for illuminating the specimen. The other two groups are directed into side-by-side reflective optical couplings 242, 244, 246 which return reflective light from the specimen that is captured by lens 302. It is noteworthy that the even division of fibers is not necessary because inequalities can easily be compensated for simply by altering circuit parameters to ratio the return reflective light from the specimen.

Figure 5:
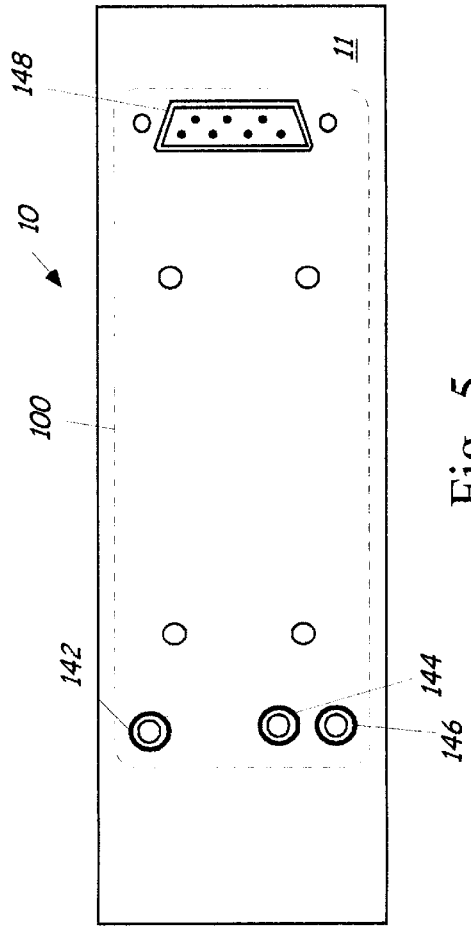
FIG. 5 is a top view of the base assembly 10.

FIG. 5 is a top view of the base assembly 10. Base assembly 10 includes a hollow elongate rectangular cabinet 11 which is pre-drilled to mount an array of three optical couplings 142, 144 and 146 at one end for mating with the corresponding optical couplings 242, 244 and 246 of connecting block 24. Cabinet 11 is also pre-drilled to expose a conventional D9 connector 148 near the other end, the D9 connector being resident on a circuit board 100 that is attached to the bottom of cabinet 11. The D9 connector 148 provides an electrical connection as necessary to the discriminating circuitry to provide logic outputs to the user's existing computer or programable logic controllers (PLCs) in order to provide feedback for process control.

Figure 6:
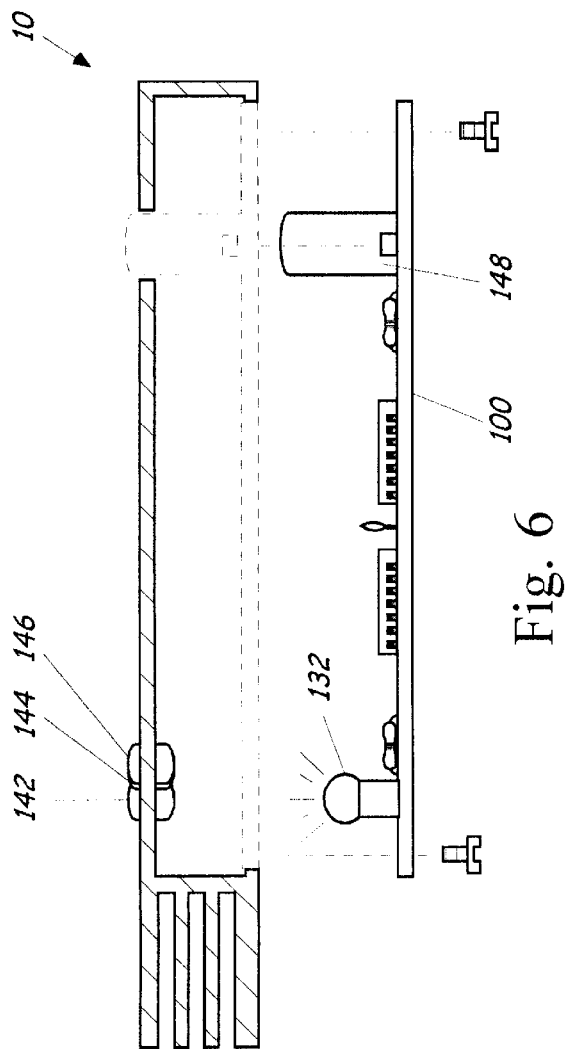
FIG. 6 is a side cross-section of the base assembly 10.

FIG. 6 is a side cross-section of the base assembly 10. Base assembly 10 is five-walled and closed at the bottom by a circuit board containing discriminator circuitry 100. The discriminator circuit board 100 fits within a shallow recess in the bottom of cabinet 11. An illumination source 132 is mounted at one end of cabinet 11 (this can be mounted on the circuit board 100). In the preferred embodiment, the illumination source 132 is a lensed-in +5 v, 5 watt (maximum) halogen bulb, although other bulbs may serve equally well. The illumination source 132 is preferably powered by a switched DC supply that can be resident on the circuit board. More specifically, a raw AC power input is taken from a power cord or through the D9 connector 148. This is rectified in a known manner, and the rectified DC output is switched and applied to the illumination source 132. This use of a switching power supply to drive the illumination source 132 power stabilizes the lamp and prevents flicker.

As can be seen, the end of the rectangular cabinet 11 proximate illumination source 132 is configured as a heat sink to dissipate the heat generated by the bulb. The illumination source 132 is positioned beneath optical coupling 142 and is coupled thereto to transmit broadband illuminating light through the transmission third of the optical fibers and outward through the hood 30 onto the sample of interest. Reflected light from the sample returns through the reflection fibers. The two sets of reflection fibers are coupled directly into the two corresponding optical couplings 144, 146. The D9 connector 148 is preferably mounted directly on the circuit board 100, and a fitted aperture is provided through the top wall of rectangular cabinet 11. This way, the D9 connector protrudes upward through the aperture when the circuit board 100 is attached (by screws or the like) to the bottom of the rectangular cabinet 11.

Figure 7:
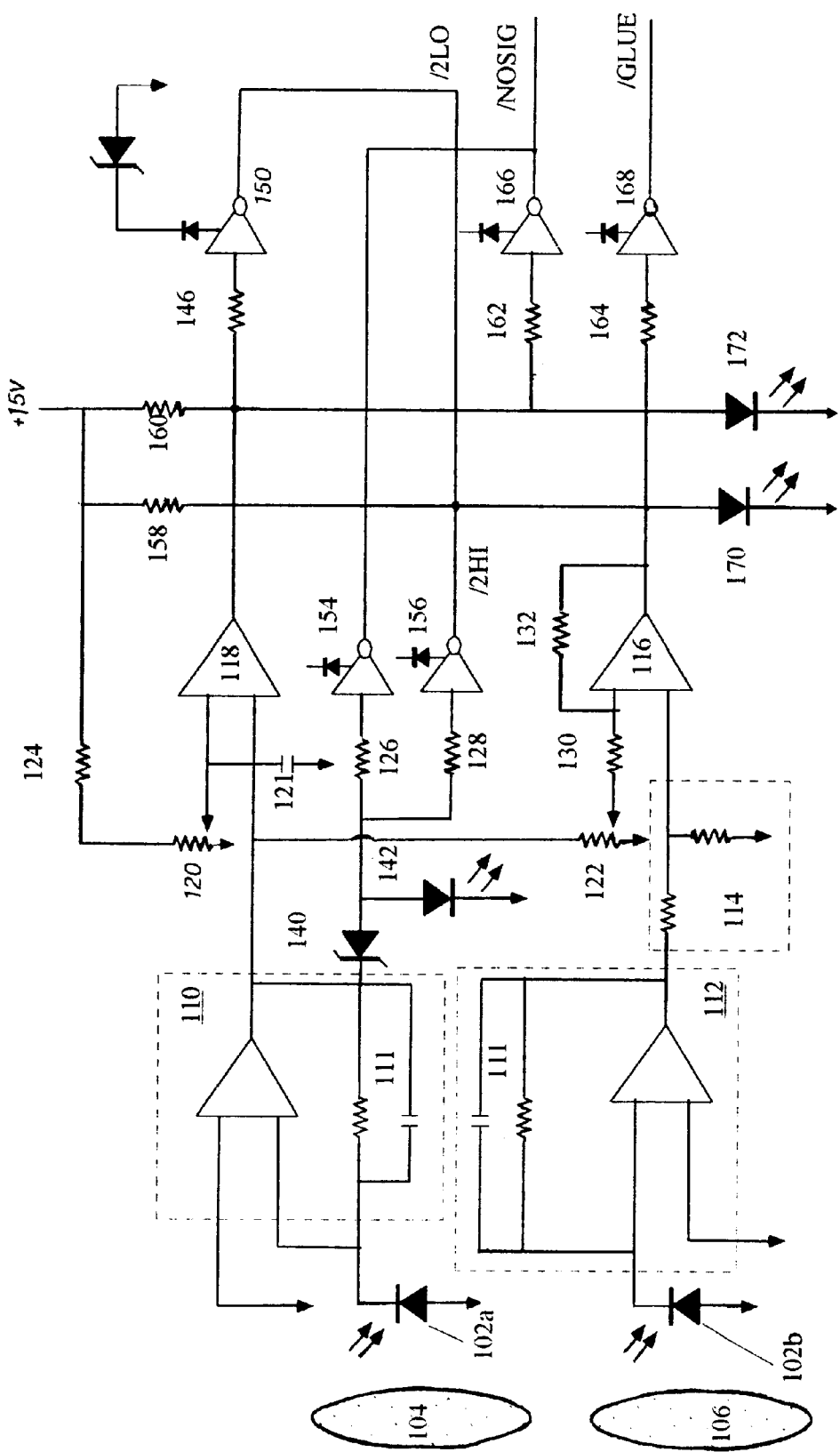
FIG. 7 is a schematic diagram of the discriminator circuitry on circuit board 100.

FIG. 7 is a schematic diagram of the discriminator circuitry that is resident on the circuit board 100. Two identical sensing photodiodes 102a & 102b are mounted behind two selective filters 104, 106, respectively. Both filters 104, 106 are conventional narrow band-pass filters that pass a selected wavelength of near- infra-red reflected light in the 600 nm to 2000 nm range. The particular band-pass characteristics of filters 104, 106 are chosen in accordance with the constituent to be discriminated. Specifically, the band-pass characteristics of filter 104 is chosen to be a first wavelength $\lambda_1$ in the near-IR range that is not significantly absorbed by the constituent of interest. The first wavelength $\lambda_1$ serves as a baseline wavelength. On the other hand, the band-pass characteristics of filter 106 is chosen to be a second wavelength $\lambda_2$ in the near-IR range that is significantly absorbed by the constituent of interest. The second wavelength $\lambda_2$ serves as the discriminator wavelength. Reflected light of the baseline wavelength $\lambda_1$ is passed by filter 104 and illuminates photodiode 102a, thereby generating a baseline signal. Reflected light of the discriminator wavelength $\lambda_2$ is passed by filter 106 and illuminates photodiode 102b, thereby generating a discriminator signal. Photodiodes 102a and 102b may be any suitable commercially available near-IR sensitive photodiodes with high speed sensing capability.

The baseline and discriminator signals are fed to the inverting inputs of detector amplifiers 110 and 112, respectively. The detector amplifiers 110 and 112 may both be commercially available op-amps (quad low-noise JFET-input op amps are suitable) set to run in transimpedance mode with feedback through resistor-capacitor bridges 111. The feedback resistors should be selected to optimize the dynamic range. The feedback capacitors should be selected to provide a 3 dB roll-off at the frequency of interest (approximately 10 kHz). The resistor-capacitor bridges 111 produce a low-pass filter. Consequently, both detector amplifiers 110 and 112 produce an output voltage that is proportional to the respective baseline wavelength $\lambda_1$ and discriminator wavelength $\lambda_2$ sensed by photodiodes 102a and 102b. The baseline and discriminator signals from detector amplifiers 110, 112, respectively, are input to comparators 118, 116 (commercially available comparators are suitable). The baseline signal from amplifier 110 is also used to provide an indication both visually and as data output for process control, both confirming the presence of baseline signal that is within low and high tolerances. The visual indication is accomplished by connecting the output of amplifier 110 through a series zener diode 140 (approximately 12 v is suitable) and LED 142 to ground. Thus, the LED 142 indicates an over-illumination fault condition (too much light coming back into detector 102a) by illuminating upon the zener 140 breaking down at 12 v. The over-illumination data output is accomplished by connecting the zener 140/ LED 142 junction to a general purpose driver 154 through resistor 126 (a conventional open-collector logic driver is suitable). The over-illumination data output/2HI is ORed with an under-illumination output/2LO (to be described), and the combined/NOSIG data is output to the D9 connector 148.

The circuit also checks the baseline against an under-illumination threshold. This is accomplished by connecting the output of amplifier 110 to the (−) input of a second identical comparator 118. The (+) input of comparator 118 is connected to an adjustable threshold setting circuit comprised of a series-connected resistor with zero-adjust 120 and fixed resistor 124 connected to a +15 v rail of the power source. This preferably establishes an under-illumination threshold less than or equal to 10% of full-scale power. The (+) input of comparator 118 is connected to filter capacitor 121. The output of comparator 118 is then connected to another general purpose driver 166 through resistor 162. A visual low-signal indication is accomplished by connecting the output of comparator 118 through LED 172 to ground. Thus, the LED 172 illuminates to indicate an under-illumination fault condition.

As mentioned above, a single combined fault data output is accomplished by connecting the output of driver 166 with the output of driver 154. This effectively ORs the outputs of LED 172 and LED 142 to provide a single/NOSIG data output line indicative of either a high or low baseline fault condition. The combined/NOSIG data is output over the D9 connector 148.

The actual discrimination of sample is accomplished by using the baseline current from detector amplifier 110 to set-up a reference baseline threshold at comparator 116. The output of amplifier 110 is connected in parallel with variable sensitivity-adjust resistor 122, and in series with resistor 130 to the (+) input of comparator 116. Resistors 130, 132 and comparator 116 define a hysteresis threshold of operation. Typical hysteresis thresholds of 3–15 mV help to stabilize the measurement process. Thus, the baseline current input to comparator 118 is compared to an adjustable threshold to provide an output indicative of whether or not there is a reflected baseline wavelength $\lambda_1$. For purposes of the present invention, comparator 116 is preferably set to fire only when the reflected discriminator wavelength $\lambda_2$ exceeds approximately one-half the reflected baseline wavelength $\lambda_1$. It has been found that this comparison gives a fast and accurate indication of the presence or absence of sample.

This should be contrasted to other spectroscopic analyzers currently on the market which try to quantify the results based on historical data. These require a complex comparison of baseline-adjusted discriminator wavelength to a database of values. The analysis is very time-consuming (and prevents real-time discrimination as with the present invention). The circuitry described above is capable of providing real-time discriminate analysis of the presence or absence of glue spot sizes as small as 0.5×0.5 mm wide and 0.5 mm high in less than 100 microseconds. Thus, the invention is fast enough to be used for real time process control of high-speed industrial glue applicators.

The output of comparator 116 is connected to a general purpose driver 168 through resistor 164, and driver 168 outputs a/GLUE signal for process control. A visual low-signal indication is accomplished by connecting the output of comparator 116 through LED 170 to ground. Thus, the LED 170 illuminates to indicate the presence of the constituent of interest (e.g., starch) in the sample (e.g., glue).

Note that the output of drivers 150 and 156 (the over-illumination data output/2HI and under-illumination output/2LO) are also connected to the output of comparator 116. This disables the/GLUE signal and invalidates the output whenever the/NOSIG data output line indicates a high or low baseline fault condition, thereby preventing erroneous readings.

The operation of the analytical discriminator and process control system according to the present invention will now be described with reference to FIGS. 1–7.

For set up, the connecting block 24 is plugged directly into the lower base 10 to complete the requisite optical couplings 242, 244, 246. To apply power and to transfer data for process control, the cable of a conventional programable logic controllers (PLC) is connected to the D9 connector on lower base 10. The flexible neck 20 should be adjusted with respect to the sample such that the light collecting lens 302 is exposed at an angle relative to the sample. The angle of the lens 302 tends to maximize diffusely reflected light energy whilst minimizing directly reflected light energy, thereby maximizing the measurable characteristics of the sample. This effectively makes the sensor unit a diffuse reflectance probe. The illuminated halogen light source 132 sends light through optical coupling 142 into a randomized one-third of the fibers of bundle 202. The transmitted light is transmitted through the lens 132 of hood 30 to the spot-sensing area (e.g., focussed on paper blanks moving along a conveyor). The present embodiment is intended to yield a 1 mm optical sensing spot size, and the sample is illuminated with the broadband light. Reflected light travels back through the lens 132 and is split by coupling it into the two remaining groups of fibers in bundle 202. The reflected light travels through the fiber bundle 202 and optical couplings 144, 146, and is filtered by the respective filters 104, 106. Filter 104 passes the baseline wavelength $\lambda_1$, while filter 106 passes the discriminator wavelength $\lambda_2$. Reflected light of the baseline wavelength $\lambda_1$ (that is passed by filter 104) illuminates photodiode 102a, thereby generating a baseline signal. Reflected light of the discriminator wavelength $\lambda_2$ is passed by filter 106 and illuminates photodiode 102b, thereby generating the discriminator signal. Both of the photodiodes 102a and 102b are connected to the inverting inputs of detector amplifiers 110 and 112, respectively. The baseline and discriminator signals from detector amplifiers 110, 112, respectively, are input to comparators 118, 116. In addition, the baseline current from detector amplifier 110 is used to set-up a reference baseline threshold at comparator 116. In essence, the baseline wavelength $\lambda_1$ (that passed by filter 104) modulates the comparator 116 threshold value which discriminates wavelength $\lambda_2$ (passed by filter 106) in direct proportion to the recovered (reflected) illumination energy. The energy of the recovered discriminator wavelength $\lambda_2$ (for the constituent of interest) is then compared against the $\lambda_1$ modulated value to determine presence or absence of the constituent of interest in the sample. The discriminator circuitry yields three visual outputs: if LED 170 is on there is glue present; if LED 172 is on there is a low signal level fault condition; if LED 142 is on there is a high signal fault condition. For real time process control, the outputs of LED 172 and LED 142 are ORed together and output on a single/NOSIG data output line. The output of LED 170 is output on a/GLUE data output line. The data outputs are conveyed to the user's existing off-board programable logic controller (PLC), computer or other controller through the D9 link from lower base 10.

A matrix of output states for each fault condition follows:

| Sample | | LEDs | | | Outputs | |
|---|---|---|---|---|---|---|
| Glue Presence | Light Condition | /2HI LED | /2LO LED | /GLUE | /NOSIG | /GLUE |
| n/a | too little | off | on | off | 1 | 0 |
| n/a | too much | on | off | off | 1 | 0 |
| 0 | nominal | off | off | off | 0 | 0 |
| 1 | nominal | off | off | off | 0 | 1 |

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. For instance, the method and apparatus can easily be adapted to discriminate on the basis of transmitted light through a sample rather than reflected light. It is to be understood, therefore, that the invention may be practiced otherwise than as specifically set forth herein.

We claim:

1. An apparatus for high speed spectroscopic constituent verification for glue lines, comprising:
    a base unit including an enclosure, a circuit board housed in said enclosure, a near-IR discriminator circuit resident on said circuit board and having a pair of selective light sensors each responsive to a particular wavelength, a light source in said enclosure, and at least three fiber optic couplings on said enclosure, two of the couplings being in optical communication with the respective light sensors and one with said light source; and
    a sensor unit including a flexible neck with a connecting block attached at one end for mating with the at least three fiber optic couplings on said base unit enclosure, and a hood assembly enclosing a light collecting and transmitting lens attached at the other end, said sensor unit also including an incoherent optical fiber bundle for transmitting light through the flexible neck via a plurality of optical fibers, a first subset of the optical fibers in said bundle being coupled between the light source in said enclosure and to said hood assembly for transmission through said lens for illumination of a sample, and a second and third subset of random optical fibers in said bundle being coupled between the lens and said light sensors for transmitting reflected light reflected back from said sample;
    whereby said near-IR discriminator circuit indicates the presence or absence of a constituent based on a difference in the reflected light received at said pair of selective light sensors.

2. The apparatus for high speed spectroscopic constituent verification according to claim 1, wherein said light source is resident on said circuit board in said enclosure.

3. The apparatus for high speed spectroscopic constituent verification according to claim 1, further comprising an output connector resident on said circuit board and connected to said near-IR discriminator circuit.

4. The apparatus for high speed spectroscopic constituent verification according to claim 3, wherein said base unit enclosure is a five-walled enclosure with an open bottom adapted to seat said circuit board.

5. The apparatus for high speed spectroscopic constituent verification according to claim 4, wherein an aperture is formed through a top wall of said base unit enclosure for exposing the output connector when the circuit board is seated in the open bottom of said housing.

6. The apparatus for high speed spectroscopic constituent verification according to claim 1, wherein said light source is a halogen bulb.

7. The apparatus for high speed spectroscopic constituent verification according to claim 6, wherein said base unit enclosure is formed with a heat sink proximate the halogen bulb.

8. The apparatus for high speed spectroscopic constituent verification according to claim 1, wherein said optical fiber bundle further comprises at least thirty fibers trifurcated at one end into subsets of at least ten fibers each.

9. The apparatus for high speed spectroscopic constituent verification according to claim 8, wherein said lens is bi-convex.

10. The apparatus for high speed spectroscopic constituent verification according to claim 9, wherein said optical fiber bundle is terminated at a distance from said lens equal to twice the focal length of said lens.

11. The apparatus for high speed spectroscopic constituent verification according to claim 10, wherein a numeric aperture of the fibers in said optical fiber bundle is matched to a numeric aperture of said lens.

12. The apparatus for high speed spectroscopic constituent verification according to claim 1, wherein said near-IR discriminator circuit resident on said circuit board further comprises a comparator having inputs connected to said sensors for indicating when a discriminator wavelength intensity sensed at one sensor exceeds approximately one-half a baseline wavelength intensity sensed at another sensor, thereby giving a fast and accurate indication of the presence or absence of sample.

13. An apparatus for high speed spectroscopic constituent verification for glue lines, comprising:
    a base unit including an enclosure, a circuit board housed in said enclosure, a near-IR discriminator circuit resident on said circuit board and having a pair of selective light sensors each responsive to a particular wavelength, and at least two fiber optic couplings on said enclosure both being in optical communication with the respective light sensors;
    a light source external to said enclosure; and
    a sensor unit including a flexible neck with a connecting block attached at one end for mating with the at least two fiber optic couplings on said enclosure on said base unit enclosure, and a hood assembly enclosing a light collecting lens attached at the other end, said sensor unit also including an incoherent optical fiber bundle for transmitting light through the flexible neck via a plurality of optical fibers, said optical fiber bundle being bifurcated and coupled between the hood assembly and to both of said light sensors for transmitting reflected light reflected back from said sample;
    whereby said near-IR discriminator circuit indicates the presence or absence of a constituent based on a difference in the reflected light received at said pair of selective light sensors.

* * * * *